United States Patent
Greene et al.

(10) Patent No.: US 7,094,564 B1
(45) Date of Patent: Aug. 22, 2006

(54) HUMAN TUMOR NECROSIS FACTOR RECEPTOR

(75) Inventors: John Greene, Gaithersburg, MD (US); Robert D. Fleischmann, Gaithersburg, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 08/469,637

(22) Filed: Jun. 6, 1995

Related U.S. Application Data

(63) Continuation-in-part of application No. PCT/US95/03216, filed on Mar. 15, 1995.

(51) Int. Cl.
G12N 15/12 (2006.01)
G12N 5/10 (2006.01)

(52) U.S. Cl. .................. 435/69.1; 435/320.1; 435/325; 536/23.5

(58) Field of Classification Search ............. 536/23.1, 536/23.5; 435/320.1, 69.1, 240.2, 325; 530/350
See application file for complete search history.

(56) References Cited

U.S. PATENT DOCUMENTS

| 5,395,760 A | 3/1995 | Smith et al. ............ 435/240.1 |
| 5,464,938 A | 11/1995 | Smith et al. ................ 530/350 |

FOREIGN PATENT DOCUMENTS

| EP | 0 585 939 | 3/1994 |
| EP | 0 816 380 | 1/1998 |
| EP | 0 816 380 A | 1/1998 |
| WO | WO 91/09045 | 6/1991 |
| WO | WO 94/09137 | 4/1994 |
| WO | WO 94/13808 | 6/1994 |
| WO | WO 96/26217 | 8/1996 |

OTHER PUBLICATIONS

George et al. (1988) Macro Molecular Sequencing and Synthesis. (Ed. by D.H. Schlesinger) Alan R. Liss, Inc., New York, pp. 127–149.*
Bowie et al. (1990) Science 247:1307–1310.*
Lewis et al. (1991) Proc. Natl. Acad. Sci. 88:2830–2834.*
Kwon et al. "TR1, a new member of the tumor necrosis factor receptor superfamily, induces fibroblast proliferation and inhibits osteoclastogenesis and bone resorption" FASEB Journal 12(10):845–854 (1998).
Simonet et al. "Osteoprotegerin: A novel secreted protein involved in the regulation of bone density" Cell 89(2):309–319 (1997).
Tsuda et al. "Isolation of a novel cytokine from human fibrobolasts that specifically inhibits osteoclastogenesis" Biochemical and Biophysical Res. Comms. 234(1):137–142 (1997).

European Search Report, Application No. 96 93 5862, dated Jan. 13, 2003.
Kohno, T. et al., "A second tumor necrosis factor receptor gene product can shed a naturally occurring tumor necrosis factor inhibitor," *Proc. Natl. Acad. Sci. USA* 87:8331–8335 (1990).
Schall, T.J. et al., "Molecular Cloning and Expression of a Receptor for Human Tumor Necrosis Factor," *Cell* 61:361–370 (1990).
Aruffo, A.A., et al., Database A–Geneseq24 on MASPAR, Accession No. R38859 (1993).
Aslanidis, C., Database EMBL–new3 on MASPAR, Accession No. X75491 (Mar. 1994).
Genexpress, Database EMBL/Genbank/DDBJ on MASPAR, Accession No. L23876 (1993).
Glasgow, E. and Schechter, N., Database EMBL–new3 on MASPAR, Accession No. L23876 (1993).
Hillier, L., et al., Database EST–STS on MASPAR, Accession No. H14106 (Jul. 1995).
Hudson, T., Database EST–STS on MASPAR, Accession No. G11923 (Oct. 1995).
Zauner, W., et al., Database EMBL–new3 on MASPAR, Accession No. X60370, X60371, X60550 (1992).
NCBI Entrez, GenBank Report, Accession No. D62967, from Fujiwara, T. et al. (Aug. 1995).
NCBI Entrez, GenBank Report, Accession No. D63118, from Fujiwara, T. et al. (Aug. 1995).
NCBI Entrez, GenBank Report, Accession No. D63125, from Fujiwara, T. et al. (Aug. 1995).
NCBI Entrez, GenBank Report, Accession No. D63126, from Fujiwara, T. et al. (Aug. 1995).
NCBI Entrez, GenBank Report, Accession No. AA296905, from Adams, M.D. et al. (Sep. 1995).
NCBI Entrez, GenBank Report, Accession No. AA296908, from Adams, M.D. et al. (Sep. 1995).

(Continued)

*Primary Examiner*—Michael Pak
(74) *Attorney, Agent, or Firm*—Human Genome Sciences, Inc.

(57) ABSTRACT

A human TNF receptor and DNA (RNA) encoding such receptor and a procedure for producing such receptor by recombinant techniques is disclosed. Also disclosed are methods for utilizing such receptor for screening for antagonists and agonists to the receptor and for ligands for the receptor. Also disclosed are methods for utilizing such agonists to inhibit the growth of tumors, to stimulate cellular differentiation, to mediate the immune response and antiviral response, to regulate growth and provide resistance to certain infections. The use of the antagonists as a therapeutic to treat autoimmune diseases, inflammation, septic shock, to inhibit graft-host reactions, and to prevent apoptosis is also disclosed. Also disclosed are diagnostic methods for detecting mutations in the nucleic acid sequence encoding the receptor and for detecting altered levels of the soluble receptor in a sample derived from a host.

51 Claims, 6 Drawing Sheets

OTHER PUBLICATIONS

NCBI Entrez, GenBank Report, Accession No. 298429, from Adams, M.D. et al. (Sep. 1995).

NCBI Entrez, GenBank Report, Accession No. H88769, from Hillier, L. et al. (Nov. 1995).

NCBI Entrez, GenBank Report, Accession No. C02463, from Okubo, K. et al. (Jul. 1996).

NCBI Entrez, GenBank Report, Accession No. AA037313, from Hillier, L. et al. (Nov. 1996).

NCBI Entrez, GenBank Report, Accession No. AA195113, from Hillier, L. et al. (May 1997).

NCBI Entrez, GenBank Report, Accession No. AA233719, from Hillier, L. et al. (Aug. 1997).

NCBI Entrez, GenBank Report, Accession No. AA706996, from Hillier, L. et al. (Dec. 1997).

NCBI Entrez, GenBank Report, Accession No. AA599841, from Jia, L. et al. (Mar. 1998).

Aggarwal, B. B. and K. Natarajan, "Tumor necrosis factors: Developments during the last decade," *Eur. Cytokine Netw.* 7(2):93–124 (Apr.–Jun. 1996).

Camerini, D. et al., "The T Cell Activation Antigen CD27 Is a Member of the Nerve Growth Factor/Tumor Necrosis Factor Receptor Gene Family," *J. Immunol.* 147(9):3165–3169 (1991).

Dürkop, H. et al., "Molecular Cloning and Expression of a New Member of the Nerve Growth Factor Receptor Family That Is Characteristic for Hodgkin's Disease," *Cell* 68:421–427 (1992).

Engelmann, H. et al., "Two Tumor Necrosis Factor–binding Proteins Purified from Human Urine. Evidence for Immunological Cross–reactivity with Cell Surface Tumor Necrosis Factor Receptors," *J. Biol. Chem.* 265(3):1531–1536 (1990).

Himmler, A. et al., "Molecular Cloning and Expression of Human and Rat Tumor Necrosis Factor Receptor Chain (p60) and Its Soluble Derivative, Tumor Necrosis Factor–Binding Protein," *DNA and Cell Biol.* 9(10):705–715 (1990).

Hohmann, H.–P. et al., "Two Different Cell Types Have Different Major Receptors for Human Tumor Necrosis Factor (TNFα)" *J. Biol. Chem.* 264(25):14927–14934 (1989).

Hsu, K. C. and M. V. Chao, "Differential Expression and Ligand Binding Properties of Tumor Necrosis Factor Receptor Chimeric Mutants," *J. Biol. Chem.* 268(22):16430–16436 (1993).

Itoh, N. et al., "The Polypeptide Encoded by the cDNA for Human Cell Surface Antigen Fas Can Mediate Apoptosis," *Cell* 66:233–243 (1991).

Johnson, D. et al., "Expression and Structure of the Human NGF Receptor," *Cell* 47:545–554 (1986).

Loetscher, H. et al., "Molecular Cloning and Expression of the Human 55 kd Tumor Necrosis Factor Receptor," *Cell* 61:351–359 (1990).

Mallett, S. et al., "Characterization of the MRC OX40 antigen of activated CD4 positive T lymphocytes—a molecule related to nerve growth factor receptor," *EMBO J.* 9(4):1063–1068 (1990).

Nophar, Y. et al., "Soluble forms of tumor necrosis factor receptors (TNF–Rs). The cDNA for the type I TNF–R, cloned using amino acid sequence data of its soluble form, encodes both the cell surface and a soluble form of the receptor," *EMBO J.* 9(10):3269–3278 (1990).

Pfeffer, K. et al., "Mice Deficient for the 55 kd Tumor Necrosis Factor Receptor Are Resistant to Endotoxic Shock, yet Succumb to L. monocytogenes Infection," *Cell* 73:457–467 (1993).

Piguet, P. F. et al., "Evolution of collagen arthritis in mice is arrested by treatment with anti–tumour necrosis factor (TNF) antibody or a recombinant soluble TNF receptor," *Immunol.* 77:510–514 (1992).

Radeke, M. J. et al., "Gene transfer and molecular cloning of the rat nerve growth factor receptor," *Nature* 325:593–597 (1987).

Smith, C. A. et al., "T2 Open Reading Frame from the Shope Fibroma Virus Encodes a Soluble Form of the TNF Receptor," *Biochem. Biophys. Res. Comm.* 176(1):335–342 (1991).

Stamenkovic, I. et al., "A B–lymphocyte activation molecule related to the nerve growth factor receptor and induced by cytokines in carcinomas," *EMBO J.* 8(5):1403–1410 (1989).

Van Ostade, X. et al., "Human tumor necrosis factor mutants with preferential binding to and activity on either the R55 or R75 receptor," *Eur. J. Biochem.* 220(3):771–779 (Mar. 1994).

Chinnaiyan, A.M. et al., "Signal Transduction by DR3, a Death Domain–Containing Receptor Related to TNFR–1 and CD95," *Science* 274:990–992 (1996).

Feinstein, E. et al., "The death domain: a module shared by proteins with diverse cellular functions," *TIBS* 20:342–344 (Sep. 1995).

Muzio, M. et al., "FLICE, A Novel FADD–Homologous ICE/CED–3–like Protease, Is Recruited to the CD95 (Fas/APO–1) Death–Inducing Signaling Complex," *Cell* 85:817–827 (1996).

Hohmann, et al., "Two Different Cell Types Have Different Major Receptors for Human Tumor Necrosis Factor (TNFα)," *The Journal of Biological Chemistry*, 264(25):14927–14934 (1989).

Leotscher, et al., "Molecular Cloning and Expression of the Human 55 kd Tumor Necrosis Factor Receptor," *Cell*, 61:351–359 (Apr. 20, 1990).

\* cited by examiner

```
                10                        30                         50
        CGCCCAGCCGCCGCCTCCAAGCCCCTGAGGTTTCCGGGGACCACAATGAACAAGTTGCTG
                                                          M  N  K  L  L
                70                        90                        110
        TGCTGCGCGCTCGTGTTTCTGGACATCTCCATTAAGTGGACCACCCAGGAAACGTTTCCT
         C  C  A  L  V  F  L  D  I  S  I  K  W  T  T  Q  E  T  F  P
               130                       150                        170
        CCAAAGTACCTTCATTATGACGAAGAAACCTCTCATCAGCTGTTGTGTGACAAATGTCCT
         P  K  Y  L  H  Y  D  E  E  T  S  H  Q  L  L  C  D  K  C  P
               190                       210                        230
        CCTGGTACCTACCTAAAACAACACTGTACAGCAAAGTGGAAGACCGTGTGCGCCCCTTGC
         P  G  T  Y  L  K  Q  H  C  T  A  K  W  K  T  V  C  A  P  C
               250                       270                        290
        CCTGACCACTACTACACAGACAGCTGGCACACCAGTGACGAGTGTCTATACTGCAGCCCC
         P  D  H  Y  Y  T  D  S  W  H  T  S  D  E  C  L  Y  C  S  P
               310                       330                        350
        GTGTGCAAGGAGCTGCAGTACGTCAAGCAGGAGTGCAATCGCACCCACAACCGCGTGTGC
         V  C  K  E  L  Q  Y  V  K  Q  E  C  N  R  T  H  N  R  V  C
               370                       390                        410
        GAATGCAAGGAAGGGCGCTACCTTGAGATAGAGTTCTGCTTGAAACATAGGAGCTGCCCT
         E  C  K  E  G  R  Y  L  E  I  E  F  C  L  K  H  R  S  C  P
               430                       450                        470
        CCTGGATTTGGAGTGGTGCAAGCTGGAACCCCAGAGCGAAATACAGTTTGCAAAAGATGT
         P  G  F  G  V  V  Q  A  G  T  P  E  R  N  T  V  C  K  R  C
               490                       510                        530
        CCAGATGGGTTCTTCTCAAATGAGACGTCATCTAAAGCACCCTGTAGAAAACACACAAAT
         P  D  G  F  F  S  N  E  T  S  S  K  A  P  C  R  K  H  T  N
               550                       570                        590
        TGCAGTGTCTTTGGTCTCCTGCTAACTCAGAAAGGAAATGCAACACACGACAACATATGT
         C  S  V  F  G  L  L  L  T  Q  K  G  N  A  T  H  D  N  I  C
               610                       630                        650
        TCCGGAAACAGTGAATCAACTCAAAAATGTGGAATAGATGTTACCCTGTGTGAGGAGGCA
         S  G  N  S  E  S  T  Q  K  C  G  I  D  V  T  L  C  E  E  A
               670                       690                        710
        TTCTTCAGGTTTGCTGTTCCTACAAAGTTTACGCCTAACTGGCTTAGTGTCTTGGTAGAC
         F  F  R  F  A  V  P  T  K  F  T  P  N  W  L  S  V  L  V  D
               730                       750                        770
        AATTTGCCTGGCACCAAAGTAAACGCAGAGAGTGTAGAGAGGATAAAACGGCAACACAGC
         N  L  P  G  T  K  V  N  A  E  S  V  E  R  I  K  R  Q  H  S
               790                       810                        830
        TCACAAGAACAGACTTTCCAGCTGCTGAAGTTATGGAAACATCAAAACAAAGACCAAGAT
         S  Q  E  Q  T  F  Q  L  L  K  L  W  K  H  Q  N  K  D  Q  D
               850                       870                        890
        ATAGTCAAGAAGATCATCCAAGATATTGACCTCTGTGAAAACAGCGTGCAGCGGCACATT
         I  V  K  K  I  I  Q  D  I  D  L  C  E  N  S  V  Q  R  H  I
               910                       930                        950
        GGACATGCTAACCTCACCTTCGAGCAGCTTCGTAGCTTGATGGAAAGCTTACCGGGAAAG
         G  H  A  N  L  T  F  E  Q  L  R  S  L  M  E  S  L  P  G  K
               970                       990                       1010
        AAAGTGGGAGCAGAAGACATTGAAAAAACAATAAAGGCATGCAAACCCAGTGACCAGATC
         K  V  G  A  E  D  I  E  K  T  I  K  A  C  K  P  S  D  Q  I
              1030                      1050                       1070
        CTGAAGCTGCTCAGTTTGTGGCGAATAAAAAATGGCGACCAAGACACCTTGAAGGGCCTA
         L  K  L  L  S  L  W  R  I  K  N  G  D  Q  D  T  L  K  G  L
              1090                      1110                       1130
        ATGCACGCACTAAAGCACTCAAAGACGTACCACTTTCCCAAAACTGTCACTCAGAGTCTA
```

FIGURE 1(A)

```
M  H  A  L  K  H  S  K  T  Y  H  F  P  K  T  V  T  Q  S  L
      1150                1170                 1190
AAGAAGACCATCAGGTTCCTTCACAGCTTCACAATGTACAAATTGTATCAGAAGTTATTT
K  K  T  I  R  F  L  H  S  F  T  M  Y  K  L  Y  Q  K  L  F
      1210                1230                 1250
TTAGAAATGATAGGTAACCAGGTCCAATCAGTAAAAATAAGCTGCTTATAACTGGAAATG
L  E  M  I  G  N  Q  V  Q  S  V  K  I  S  C  L  *
      1270                1290                 1310
GCCATTGAGCTGTTTCCTCACAATTGGCGAGATCCCATGGATGAGTAAACTGTTTCTCAG
      1330                1350                 1370
GCACTTGAGGCTTTCAGTGATATCTTTCTCATTACCAGTGACTAATTTTGCCACAGGGTA
      1390                1410                 1430
CTAAAAGAAACTATGATGTGGAGAAAGGACTAACATCTCCTCCAATAAACCCCAAATGGT
      1450                1470                 1490
TAATCCAACTGTCAGATCTGGATCGTTATCTACTGACTATATTTTCCCTTATTACTGCTT
      1510
GCAGTAATTCAACTGGAAAAAAAAAAA
```

FIGURE 1(B)

```
  1 .....MNKLLCCALVFLDISIKWTTQETFPP.........KYLHYDEETS  36
         :   |..:|  .::.  .   :..| .|.|_      :. .| ::|.
  1 MAPVAVWAALAVGLELWAAAHALPAQVAFTPYAPEPGSTCRLREYYDQTA  50

37 HQLLCDKCPPGTYLKQHCTAKWKTVCAPCPDHYYTDSWHTSDECLYCSPV  86
    |: |.||.|| . |  ||  ...|||..|.|  ||: |:  .||| |:.
 51 .QMCCSKCSPGQHAKVFCTKTSDTVCDSCEDSTYTQLWNWVPECLSCGSR  99

87 CKELQYVKQECNRTHNRVCECKEGRYLEIE......FCLKHRSCPPGFGV 130
    |.. |  .|.|.|.:||:|.|:.|:|  .:.      :| . |.|.||||
100 CSSDQVETQACTREQNRICTCRPGWYCALSKQEGCRLCAPLRKCRPGFGV 149

131 VQAGTPERNTVCKRCPDGFFSNETSSKAPCRKHTNCSVFGLLLTQKGNAT 180
    ..:||...:.|||.|:.| |||.|||.. ||.|  |.|.:: .|||.
150 ARPGTETSDVVCKPCAPGTFSNTTSSTDICRPHQICNVVAI....PGNAS 195

181 HDNIC...................SGNSESTQKCGIDVTLCEEAFF... 207.
    |.:|                    |..|: ||... . | ....|:
196 MDAVCTSTSPTRSMAPGAVHLPQPVSTRSQHTQPTPEPSTAPSTSFLLPM 245

208 ..........RFAVPTKFTPNWLSVLVDNLPGTKVNAESVERIKR.... 242
              ||:|. :...  . :: | . ||.  :..:|:
246 GPSPPAEGSTGDFALPVGLIVG..VTALGLLIIGVVNCVIMTQVKKKPLC 293

243 .QHSSQEQTFQLLKLWKHQNKDQDIV.....KKIIQDIDLCENSVQRHIG 286
     |:... . :.   |  :  |..:|: :      ..  .::  :...::|: .
294 LQREAKVPHLPADKARGTQGPEQQHLLITAPSSSSSSLESSASALDRRAP 343

287 HANLTFEQLRSLMESLPGK...KVGAEDIEKTIKACKPSDQILKLLSLWR 333
    | . | .:: .| :|.  ..|..| ... .:.... .: :: ..
344 TRNQP..QAPGVEASGAGEARASTGSSDSSPGGHGTQVNVTCIVNVCSSS 391

334 IKNGDQDTLKGLMHALKHSKTYHFPKTVTQSLKKTIRFLHS.....FTMY 378
    ..::  ..  :   : ..|... ||.  .:.|.   ::|       |:.
392 DHSSQCSSQASSTMGDTDSSPSESPKDEQVPFSKEECAFRSQLETPETLL 441

379 KLYQKLFLEMIGNQVQSVKISCL. 401
    :.  |.: | . .::| | |
442 GSTEEKPLPL.GVPDAGMKPS... 461
```

```
                                                                            50
tnfr2.msf{TNFR2_LIKE}   .....MNKLL CCALVFLDIS IKWTQETFP P.......... KYLHYDEETS
tnfr2.msf{TNR2_HUMAN}   MAPVAVWAAL AVGLELWAAA HALPAQVAFT PYAPEPGSTC RLREYYDQTA
            Consensus   ---------L ---------- ------Q--F P---------- ----Y---T-

100
tnfr2.msf{TNFR2_LIKE}   HQLLCDKCPP GTYLKQHCTA KWKTVCAPCP DHYYTDSWHT SDECLYCSPV
tnfr2.msf{TNR2_HUMAN}   .QMCCSKCSP GQHAKVFCTK TSDTVCDSCE DSTYTQLWNW VPECLSCGSR
            Consensus   -Q--C--KC-P G-----C-- ---TVC----- D---YT----W- --ECL-C---

150
tnfr2.msf{TNFR2_LIKE}   CKELQYVKQE CNRTHNRVCE CKEGRYLEIE ......FCLK HRSCPPGFGV
tnfr2.msf{TNR2_HUMAN}   CSSDQVETQA CTREQNRICT CRPGWYCALS KQEGCRLCAP LRKCRPGFGV
            Consensus   C----Q----Q- --C-R--NR-C- C---G--Y---- ---------- -R-C--PGFGV 200
tnfr2.msf{TNFR2_LIKE}   VQAGTPERNT VCKRCPDGFF SNETSSKAPC RKHTNCSVFG LLLTQKGNAT
tnfr2.msf{TNR2_HUMAN}   ARPGTETSDV VCKPCAPGTF SNTTSSTDIC RPHQICNVVA I....PGNAS
            Consensus   ---GT----- VCK-C--G-F SN-TSS----C R-H--C-V-- -----GNA- 250
tnfr2.msf{TNFR2_LIKE}   HDNIC..... .......... .....SGNSE STQKCGIDVT LCEEAFF...
tnfr2.msf{TNR2_HUMAN}   RDAVCTSTSP TRSMAPGAVH LPQPVSTRSQ HTQPTPEPST APSTSFLLPM
            Consensus   -D--C----- ---------- ------S--S- --TQ------T ------F---
```

MATCH WITH FIG. 2B

FIG. 2B

MATCH WITH FIG. 2A

```
                         251                                                            300
lfr2.msf{TNFR2_LIKE}     .........  .RFAVPTKFT  PNWLSVLVDN  LPGTKVNAES  VERIKR....
lfr2.msf{TNR2_HUMAN}     GPSPPAEGST  GDFALPVGLI  VG..VTALGL  LIIGVVNCVI  MTQVKKKPLC
            Consensus    ----------  ---FA-P---  ----------  L-----VN--  -----K----

301                                                            350
lfr2.msf{TNFR2_LIKE}     .QHSSQEQTF  QLLKLWKHQN  KDQDIV....  .KKIIQDIDL  CENSVQRHIG
lfr2.msf{TNR2_HUMAN}     LQREAKVPHL  PADKARGTQG  PEQQHLLITA  PSSSSSSLES  SASALDRRAP
            Consensus    -Q--------  ---K------  ---Q------  ----------  -------R--

351                                                            400
lfr2.msf{TNFR2_LIKE}     HANLTFEQLR  SLMESLPGKK  VGAEDIEKTI  KACKPSDQIL  KLLSLWRIKN
lfr2.msf{TNR2_HUMAN}     TRNQP..QAP  GVEASGAGEA  RASTGSSDSS  PGGHGTQ..V  NVTCIVNVCS
            Consensus    --N----Q--  ----S--G--  ----------  ----------  ----------

401                                                            450
lfr2.msf{TNFR2_LIKE}     GDQDTLKGLM  HALKHSKTYH  FPTNCHSESK  EDHQVPSQLH  NVQIVSEVIF
lfr2.msf{TNR2_HUMAN}     SSDHSSQCSS  QA...SSTMG  DTDSSPSESP  KDEQVPFSKE  ECAFRSQLET
            Consensus    ----------  -A----S-T-  ------SES-  --D-QVP---  -----S----

451         475
lfr2.msf{TNFR2_LIKE}     RNDR......  ..........
lfr2.msf{TNR2_HUMAN}     PETLLGSTEE  KPLPLGVPDA  GMKPS
            Consensus    ----------  ----------
```

MATCH WITH FIG. 2C

FIG. 2C

MATCH WITH FIG. 2B

```
Query:  38  QLLCDKCPPGTYLKQHCTAKWKTVCAPCPDHYYTDSWHTSDECLYCSPVCKELQYVKQEC  97
            Q+ C KC PG + K CT    TVC  C D YT W+  ECL C    C  Q    Q C
Sbjct:  29  QMCCSKCSPGQHAKVFCTKTSDTVCDSCEDSTYTQLMNWVPECLSGGSRCSSDQVETQAC  88

Query:  98  NRTHNRVCECKEGRYLEIEFCLKHRSCPP  126
            R  NR+C C+ G Y +     R C P
Sbjct:  89  TREQNRICTCRPGWYCALSKQEGCRLCAP  117

Query: 118  CLKHRSCPPGFGVVQAGTPERNTVCKRCPDGFFSNETSSKAPCRKHTNCSVFGL  171
            C   R C PGFGV + GT     + VCK C  G F+N TSS    CR H C+V +
Sbjct: 115  CAPLRKCRPGFGVARPGTETSDVVCKPCAPGTFSNTTSSTDICRPHQICNVVAI  168

Query: 177  GNATHDNICSGNS  189
            GNA+ D +C+ S
Sbjct: 170  GNASMDAVCTSTS  182

Query: 363  SESKEDHQVP  372
            SES +D QVP
Sbjct: 391  SESPKDEQVP  400
```

US 7,094,564 B1

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 1527 base pairs
      (B) TYPE: nucleic acid
      (C) STRANDEDNESS: double
      (D) TOPOLOGY: linear (ii) MOLECULE TYPE: DNA (genomic)

(ix) FEATURE:
      (A) NAME/KEY: CDS
      (B) LOCATION: 46..1248

(ix) FEATURE:
      (A) NAME/KEY: sig_peptide
      (B) LOCATION: 46..106

(ix) FEATURE:
      (A) NAME/KEY: mat_peptide
      (B) LOCATION: 109..1248

(xi) SEQUENCE DESCRIPTION: SEQ ID NO:1:

```
CGCCCAGCCG CCGCCTCCAA GCCCCTGAGG TTTCCGGGGA CCACA ATG AAC AAG           54
                                                Met Asn Lys
                                                -21 -20

TTG CTG TGC TGC GCG CTC GTG TTT CTG GAC ATC TCC ATT AAG TGG ACC        102
Leu Leu Cys Cys Ala Leu Val Phe Leu Asp Ile Ser Ile Lys Trp Thr
            -15                 -10                 -5

ACC CAG GAA ACG TTT CCT CCA AAG TAC CTT CAT TAT GAC GAA GAA ACC        150
Thr Gln Glu Thr Phe Pro Pro Lys Tyr Leu His Tyr Asp Glu Glu Thr
          1               5                  10

TCT CAT CAG CTG TTG TGT GAC AAA TGT CCT CCT GGT ACC TAC CTA AAA        198
Ser His Gln Leu Leu Cys Asp Lys Cys Pro Pro Gly Thr Tyr Leu Lys
 15                 20              25                  30
```

-continued

```
CAA CAC TGT ACA GCA AAG TGG AAG ACC GTG TGC GCC CCT TGC CCT GAC      246
Gln His Cys Thr Ala Lys Trp Lys Thr Val Cys Ala Pro Cys Pro Asp
            35                  40                  45

CAC TAC TAC ACA GAC AGC TGG CAC ACC AGT GAC GAG TGT CTA TAC TGC      294
His Tyr Tyr Thr Asp Ser Trp His Thr Ser Asp Glu Cys Leu Tyr Cys
        50                  55                  60

AGC CCC GTG TGC AAG GAG CTG CAG TAC GTC AAG CAG GAG TGC AAT CGC      342
Ser Pro Val Cys Lys Glu Leu Gln Tyr Val Lys Gln Glu Cys Asn Arg
            65                  70                  75

ACC CAC AAC CGC GTG TGC GAA TGC AAG GAA GGG CGC TAC CTT GAG ATA      390
Thr His Asn Arg Val Cys Glu Cys Lys Glu Gly Arg Tyr Leu Glu Ile
        80                  85                  90

GAG TTC TGC TTG AAA CAT AGG AGC TGC CCT CCT GGA TTT GGA GTG GTG      438
Glu Phe Cys Leu Lys His Arg Ser Cys Pro Pro Gly Phe Gly Val Val
 95                 100                 105                 110

CAA GCT GGA ACC CCA GAG CGA AAT ACA GTT TGC AAA AGA TGT CCA GAT      486
Gln Ala Gly Thr Pro Glu Arg Asn Thr Val Cys Lys Arg Cys Pro Asp
            115                 120                 125

GGG TTC TTC TCA AAT GAG ACG TCA TCT AAA GCA CCC TGT AGA AAA CAC      534
Gly Phe Phe Ser Asn Glu Thr Ser Ser Lys Ala Pro Cys Arg Lys His
        130                 135                 140

ACA AAT TGC AGT GTC TTT GGT CTC CTG CTA ACT CAG AAA GGA AAT GCA      582
Thr Asn Cys Ser Val Phe Gly Leu Leu Leu Thr Gln Lys Gly Asn Ala
            145                 150                 155

ACA CAC GAC AAC ATA TGT TCC GGA AAC AGT GAA TCA ACT CAA AAA TGT      630
Thr His Asp Asn Ile Cys Ser Gly Asn Ser Glu Ser Thr Gln Lys Cys
        160                 165                 170

GGA ATA GAT GTT ACC CTG TGT GAG GAG GCA TTC TTC AGG TTT GCT GTT      678
Gly Ile Asp Val Thr Leu Cys Glu Glu Ala Phe Phe Arg Phe Ala Val
175                 180                 185                 190

CCT ACA AAG TTT ACG CCT AAC TGG CTT AGT GTC TTG GTA GAC AAT TTG      726
Pro Thr Lys Phe Thr Pro Asn Trp Leu Ser Val Leu Val Asp Asn Leu
            195                 200                 205

CCT GGC ACC AAA GTA AAC GCA GAG AGT GTA GAG AGG ATA AAA CGG CAA      774
Pro Gly Thr Lys Val Asn Ala Glu Ser Val Glu Arg Ile Lys Arg Gln
        210                 215                 220

CAC AGC TCA CAA GAA CAG ACT TTC CAG CTG CTG AAG TTA TGG AAA CAT      822
His Ser Ser Gln Glu Gln Thr Phe Gln Leu Leu Lys Leu Trp Lys His
            225                 230                 235

CAA AAC AAA GAC CAA GAT ATA GTC AAG AAG ATC ATC CAA GAT ATT GAC      870
Gln Asn Lys Asp Gln Asp Ile Val Lys Lys Ile Ile Gln Asp Ile Asp
        240                 245                 250

CTC TGT GAA AAC AGC GTG CAG CGG CAC ATT GGA CAT GCT AAC CTC ACC      918
Leu Cys Glu Asn Ser Val Gln Arg His Ile Gly His Ala Asn Leu Thr
255                 260                 265                 270

TTC GAG CAG CTT CGT AGC TTG ATG GAA AGC TTA CCG GGA AAG AAA GTG      966
Phe Glu Gln Leu Arg Ser Leu Met Glu Ser Leu Pro Gly Lys Lys Val
            275                 280                 285

GGA GCA GAA GAC ATT GAA AAA ACA ATA AAG GCA TGC AAA CCC AGT GAC     1014
Gly Ala Glu Asp Ile Glu Lys Thr Ile Lys Ala Cys Lys Pro Ser Asp
        290                 295                 300

CAG ATC CTG AAG CTG CTC AGT TTG TGG CGA ATA AAA AAT GGC GAC CAA     1062
Gln Ile Leu Lys Leu Leu Ser Leu Trp Arg Ile Lys Asn Gly Asp Gln
            305                 310                 315

GAC ACC TTG AAG GGC CTA ATG CAC GCA CTA AAG CAC TCA AAG ACG TAC     1110
Asp Thr Leu Lys Gly Leu Met His Ala Leu Lys His Ser Lys Thr Tyr
        320                 325                 330

CAC TTT CCC AAA ACT GTC ACT CAG AGT CTA AAG AAG ACC ATC AGG TTC     1158
His Phe Pro Lys Thr Val Thr Gln Ser Leu Lys Lys Thr Ile Arg Phe
335                 340                 345                 350
```

```
CTT CAC AGC TTC ACA ATG TAC AAA TTG TAT CAG AAG TTA TTT TTA GAA    1206
Leu His Ser Phe Thr Met Tyr Lys Leu Tyr Gln Lys Leu Phe Leu Glu
            355                 360                 365

ATG ATA GGT AAC CAG GTC CAA TCA GTA AAA ATA AGC TGC TTA            1248
Met Ile Gly Asn Gln Val Gln Ser Val Lys Ile Ser Cys Leu
            370                 375                 380

TAACTGGAAA TGGCCATTGA GCTGTTTCCT CACAATTGGC GAGATCCCAT GGATGAGTAA  1308

ACTGTTTCTC AGGCACTTGA GGCTTTCAGT GATATCTTTC TCATTACCAG TGACTAATTT  1368

TGCCACAGGG TACTAAAAGA AACTATGATG TGGAGAAAGG ACTAACATCT CCTCCAATAA  1428

ACCCCAAATG GTTAATCCAA CTGTCAGATC TGGATCGTTA TCTACTGACT ATATTTTCCC  1488

TTATTACTGC TTGCAGTAAT TCAACTGGAA AAAAAAAA                         1527
```

(2) INFORMATION FOR SEQ ID NO:2:

(i) SEQUENCE CHARACTERISTICS:
        (A) LENGTH: 401 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asn Lys Leu Leu Cys Cys Ala Leu Val Phe Leu Asp Ile Ser Ile
-21     -20             -15                 -10

Lys Trp Thr Thr Gln Glu Thr Phe Pro Pro Lys Tyr Leu His Tyr Asp
-5              1               5                   10

Glu Glu Thr Ser His Gln Leu Leu Cys Asp Lys Cys Pro Pro Gly Thr
                15              20                  25

Tyr Leu Lys Gln His Cys Thr Ala Lys Trp Lys Thr Val Cys Ala Pro
            30              35              40

Cys Pro Asp His Tyr Tyr Thr Asp Ser Trp His Thr Ser Asp Glu Cys
            45              50              55

Leu Tyr Cys Ser Pro Val Cys Lys Glu Leu Gln Tyr Val Lys Gln Glu
60              65              70                          75

Cys Asn Arg Thr His Asn Arg Val Cys Glu Cys Lys Glu Gly Arg Tyr
                80              85                  90

Leu Glu Ile Glu Phe Cys Leu Lys His Arg Ser Cys Pro Pro Gly Phe
                95              100                 105

Gly Val Val Gln Ala Gly Thr Pro Glu Arg Asn Thr Val Cys Lys Arg
            110             115             120

Cys Pro Asp Gly Phe Phe Ser Asn Glu Thr Ser Ser Lys Ala Pro Cys
            125             130             135

Arg Lys His Thr Asn Cys Ser Val Phe Gly Leu Leu Leu Thr Gln Lys
140             145             150                         155

Gly Asn Ala Thr His Asp Asn Ile Cys Ser Gly Asn Ser Glu Ser Thr
                160             165                 170

Gln Lys Cys Gly Ile Asp Val Thr Leu Cys Glu Glu Ala Phe Phe Arg
            175             180             185

Phe Ala Val Pro Thr Lys Phe Thr Pro Asn Trp Leu Ser Val Leu Val
            190             195             200

Asp Asn Leu Pro Gly Thr Lys Val Asn Ala Glu Ser Val Glu Arg Ile
            205             210             215

Lys Arg Gln His Ser Ser Gln Glu Gln Thr Phe Gln Leu Leu Lys Leu
220             225             230                         235
```

```
Trp Lys His Gln Asn Lys Asp Gln Asp Ile Val Lys Ile Ile Gln
            240             245             250

Asp Ile Asp Leu Cys Glu Asn Ser Val Gln Arg His Ile Gly His Ala
            255             260             265

Asn Leu Thr Phe Glu Gln Leu Arg Ser Leu Met Glu Ser Leu Pro Gly
            270             275             280

Lys Lys Val Gly Ala Glu Asp Ile Glu Lys Thr Ile Lys Ala Cys Lys
            285             290             295

Pro Ser Asp Gln Ile Leu Lys Leu Leu Ser Leu Trp Arg Ile Lys Asn
300             305             310             315

Gly Asp Gln Asp Thr Leu Lys Gly Leu Met His Ala Leu Lys His Ser
                320             325             330

Lys Thr Tyr His Phe Pro Lys Thr Val Thr Gln Ser Leu Lys Lys Thr
            335             340             345

Ile Arg Phe Leu His Ser Phe Thr Met Tyr Lys Leu Tyr Gln Lys Leu
            350             355             360

Phe Leu Glu Met Ile Gly Asn Gln Val Gln Ser Val Lys Ile Ser Cys
            365             370             375

Leu
380

(2) INFORMATION FOR SEQ ID NO:3:

(i) SEQUENCE CHARACTERISTICS:
        (A) LENGTH: 461 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:3:

Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
            20              25                  30

Ala Pro Glu Pro Gly Ser Thr Cys Arg Leu Arg Glu Tyr Tyr Asp Gln
            35              40                  45

Thr Ala Gln Met Cys Cys Ser Lys Cys Ser Pro Gly Gln His Ala Lys
            50              55                  60

Val Phe Cys Thr Lys Thr Ser Asp Thr Val Cys Asp Ser Cys Glu Asp
65              70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100             105                 110

Glu Gln Asn Arg Ile Cys Thr Cys Arg Pro Gly Trp Tyr Cys Ala Leu
            115             120                 125

Ser Lys Gln Glu Gly Cys Arg Leu Cys Ala Pro Leu Arg Lys Cys Arg
            130             135                 140

Pro Gly Phe Gly Val Ala Arg Pro Gly Thr Glu Thr Ser Asp Val Val
145             150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180             185                 190
```

```
Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Ala Glu Gly Ser Thr Gly
            245                 250                 255

Asp Phe Ala Leu Pro Val Gly Leu Ile Val Gly Val Thr Ala Leu Gly
            260                 265                 270

Leu Leu Ile Ile Gly Val Val Asn Cys Val Ile Met Thr Gln Val Lys
        275                 280                 285

Lys Lys Pro Leu Cys Leu Gln Arg Glu Ala Lys Val Pro His Leu Pro
    290                 295                 300

Ala Asp Lys Ala Arg Gly Thr Gln Gly Pro Glu Gln Gln His Leu Leu
305                 310                 315                 320

Ile Thr Ala Pro Ser Ser Ser Ser Ser Leu Glu Ser Ser Ala Ser
            325                 330                 335

Ala Leu Asp Arg Arg Ala Pro Thr Arg Asn Gln Pro Gln Ala Pro Gly
            340                 345                 350

Val Glu Ala Ser Gly Ala Gly Glu Ala Arg Ala Ser Thr Gly Ser Ser
        355                 360                 365

Asp Ser Ser Pro Gly Gly His Gly Thr Gln Val Asn Val Thr Cys Ile
    370                 375                 380

Val Asn Val Cys Ser Ser Ser Asp His Ser Ser Gln Cys Ser Ser Gln
385                 390                 395                 400

Ala Ser Ser Thr Met Gly Asp Thr Asp Ser Ser Pro Ser Glu Ser Pro
            405                 410                 415

Lys Asp Glu Gln Val Pro Phe Ser Lys Glu Glu Cys Ala Phe Arg Ser
            420                 425                 430

Gln Leu Glu Thr Pro Glu Thr Leu Leu Gly Ser Thr Glu Glu Lys Pro
        435                 440                 445

Leu Pro Leu Gly Val Pro Asp Ala Gly Met Lys Pro Ser
    450                 455                 460

(2) INFORMATION FOR SEQ ID NO:4:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

GCCAGAGGAT CCGAAACGTT TCCTCCAAAG TAC                          33

(2) INFORMATION FOR SEQ ID NO:5:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA
```

(xi) SEQUENCE DESCRIPTION: SEQ ID NO:5:

CGGCTTCTAG AATTACCTAT CATTTCTAAA AAT     33

(2) INFORMATION FOR SEQ ID NO:6:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

GCGCGGATCC ATGAACAAGT TGCTGTGCTG C     31

(2) INFORMATION FOR SEQ ID NO:7:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

GCGCTCTAGA TTACCTATCA TTTCTAAAAA TAAC     34

(2) INFORMATION FOR SEQ ID NO:8:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

GCGCGGTACC TCAGTGGTTT GGGCTCCTCC C     31

(2) INFORMATION FOR SEQ ID NO:9:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

GCCAGAGGAT CCGCCACCAT GAACAAGTTG CTGTGCTGC     39

(2) INFORMATION FOR SEQ ID NO:10:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

CGGCTTCTAG AATCAAGCGT AGTCTGGGAC GTCGTATGGG TACCTATCAT TTCTAAAAAT     60

HUMAN TUMOR NECROSIS FACTOR RECEPTOR

CROSS REFERENCE TO RELATED APPLICATIONS

The present application is a continuation-in-part of PCT/US95/03216, filed Mar. 15, 1995.

FIELD OF THE INVENTION

This invention relates to newly identified polynucleotides, polypeptides encoded by such polynucleotides, the use of such polynucleotides and polypeptides, as well as the production of such polynucleotides and polypeptides. The polypeptide of the present invention has been putatively identified as a Tumor Necrosis Factor receptor, and more particularly as a type 2 Tumor Necrosis Factor Receptor. The polypeptide of the present invention will hereinafter be referred to as "TNF receptor". The invention also relates to inhibiting the receptor.

RELATED ART

Human tumor necrosis factors α (TNF-α) and β (TNF-β or lymphotoxin) are related members of a broad class of polypeptide mediators, which includes the interferons, interleukins and growth factors, collectively called cytokines (Beutler, B. and Cerami, A., Annu. Rev. Immunol., 7:625–655 (1989)).

Tumor necrosis factor (TNF-α and TNF-β) was originally discovered as a result of its anti-tumor activity, however, now it is recognized as a pleiotropic cytokine playing important roles in a host of biological processes and pathologies. To date, there are eight known members of the TNF-related cytokine family, TNF-α, TNF-β (lymphotoxin-α), LT-β, and ligands for the Fas receptor, CD30, CD27, CD40 and 4-1BB receptors. These proteins have conserved C-terminal sequences and variable N-terminal sequences which are often used as membrane anchors, with the exception of TNF-β. Both TNF-α and TNF-β function as homotrimers when they bind to TNF receptors.

TNF is produced by a number of cell types, including monocytes, fibroblasts, T cells, natural killer (NK) cells and predominately by activated machrophages. TNF-α has been reported to have a role in the rapid necrosis of tumors, immunostimulation, autoimmune disease, graft rejection, producing an anti-viral response, septic shock, cerebral malaria, cytotoxicity, protection against deleterious effects of ionizing radiation produced during a course of chemotherapy, such as denaturation of enzymes, lipid peroxidation and DNA damage (Nata et al, J. Immunol. 136 (7):2483 (1987)), growth regulation, vascular endothelium effects and metabolic effects. TNF-α also triggers endothelial cells to secrete various factors, including PAI-1, IL-1, GM-CSF and IL-6 to promote cell proliferation. In addition, TNF-α up-regulates various cell adhesion molecules such as E-Selectin, ICAM-1 and VCAM-1. TNF-α and the Fas ligand have also been shown to induce programmed cell death.

A related molecule, lymphotoxin (LT, also referred to as TNF-β), which is produced by activated lymphocytes shows a similar but not identical spectrum of biological activities as TNF. Two different types of LT have been found, LT-α and LT-β.LT-α has many activities, including tumor necrosis, induction of an antiviral state, activation of polymorphonuclear leukocytes, induction of class I major histocompatibility complex antigens on endothelial cells, induction of adhesion molecules on endothelium and growth hormone stimulation (Ruddle, N. and Homer, R., Prog. Allergy, 40:162–182 (1988)).

The first step in the induction of the various cellular responses mediated by TNF or LT is their binding to specific cell surface or soluble receptors. Two distinct TNF receptors of approximately 55-KDa (TNF-R1) and 75-KDa (TNF-R2) have been identified (Hohman, H. P. et al., J. Biol. Chem., 264:14927–14934 (1989)), and human and mouse cDNAs corresponding to both receptor types have been isolated and characterized (Loetscher, H. et al., Cell, 61:351 (1990)). Both TNF-Rs share the typical structure of cell surface receptors including extracellular, transmembrane and intracellular regions.

These molecules exist not only in cell bound forms, but also in soluble forms, consisting of the cleaved extra-cellular domains of the intact receptors (Nophar et al., EMBO Journal, 9 (10):3269–76 (1990)). The extracellular domains of TNF-R1 and TNF-R2 share 28% identity and are characterized by four repeated cysteine-rich motifs with significant intersubunit sequence homology. The majority of cell types and tissues appear to express both TNF receptors and both receptors are active in signal transduction, however, they are able to mediate distinct cellular responses. Further, TNF-R2 was shown to exclusively mediate human T cell proliferation by TNF as shown in PCT WO 94/09137.

TNF-R1 dependent responses include accumulation of C-FOS, IL-6, and manganese superoxide dismutase mRNA, prostaglandin E2 synthesis, IL-2 receptor and MHC class I and II cell surface antigen expression, growth inhibition, and cytotoxicity. TNF-R1 also triggers second messenger systems such as phospholipase $A_2$, protein kinase C, phosphatidylcholine specific phospholipase C and sphingomyelinase (Pfeffer, K. et al., Cell, 73:457–4.67 (1993)).

SUMMARY OF THE INVENTION

The receptor polypeptide of the present invention binds TNF, and in particular, TNF-β. Further, the TNF receptor may also bind other ligands, including but not limited to Nerve Growth Factor, due to homology to a family of receptors and antigens which are involved in other critical biological processes. This family shows highly conserved cysteine residues and includes the low affinity NGF receptor, which plays an important role in the regulation of growth and differentiation of nerve cells, the Fas receptor also called APO, a receptor which is involved is signalling for apoptosis and which, based on a study with mice deficient in its function, seems to play an important role in the etiology of a lupus-like disease, the TNF-R1, the B cell antigen CD40, and the T cell activation antigen CD27.

In accordance with one aspect of the present invention, there is provided a novel mature polypeptide which is a putative TNF receptor, as well as fragments, analogs and derivatives thereof. The polypeptide of the present invention is of human origin.

In accordance with another aspect of the present invention, there are provided isolated nucleic acid molecules encoding the polypeptide of the present invention, including mRNAs, DNAs, cDNAs, genomic DNA as well as antisense analogs thereof and biologically active and diagnostically or therapeutically useful fragments thereof.

In accordance with yet a further aspect of the present invention, there is provided a process for producing such polypeptides by recombinant techniques which comprises culturing recombinant prokaryotic and/or eukaryotic host cells, containing a nucleic acid sequence encoding a polypeptide of the present invention, under conditions promoting expression of said protein and subsequent recovery of said protein.

In accordance with yet a further aspect of the present invention, there is provided a process for utilizing such polypeptide, or polynucleotide encoding such polypeptide to screen for receptor antagonists and/or agonists and/or receptor ligands.

In accordance with yet a further aspect of the present invention, there are provided nucleic acid probes comprising nucleic acid molecules of sufficient length to specifically hybridize to the polypeptide of the present invention.

In accordance with still another aspect of the present invention, there is provided a process of using such agonists for treating conditions related to insufficient TNF receptor activity, for example, to inhibit tumor growth, to stimulate human cellular proliferation, e.g., T-cell proliferation, to regulate the immune response and antiviral responses, to protect against the effects of ionizing radiation, to protect against chlamidiae infection, to regulate growth and to treat immunodeficiencies such as is found in HIV.

In accordance with another aspect of the present invention, there is provided a process of using such antagonists for treating conditions associated with over-expression of the TNF receptor, for example, for treating T-cell mediated autoimmune diseases such as AIDS, septic shock, cerebral malaria, graft rejection, cytotoxicity, cachexia, apoptosis and inflammation.

These and other aspects of the present invention should be apparent to those skilled in the art from the teachings herein.

The following drawings are illustrative of embodiments of the invention and are not meant to limit the scope of the invention as encompassed by the claims,

BRIEF DESCRIPTION OF THE FIGURES

FIG. 1 shows the cDNA sequence (SEQ ID NO:1) and corresponding deduced amino acid sequence (SEQ ID NO:2) of the polypeptide of the present invention. The initial 21 amino acids represent the putative leader sequence and are underlined. The standard one-letter abbreviations for amino acids are used. Sequencing was performed using a 373 automated DNA sequencer (Applied Biosystems, Inc.). Sequencing accuracy is predicted to be greater than 97% accurate.

FIG. 2 illustrates an amino acid sequence alignment of the polypeptide of the present invention (upper line) (SEQ ID NO:2) and the human type 2 TNF receptor (lower line) (SEQ ID NO:3).

DETAILED DESCRIPTION OF THE INVENTION

The term "gene" or "cistron" means the segment of involved in producing a polypeptide chain; it includes regions preceding and following the coding region (leader and trailer) as well as intervening sequences (introns) between individual coding segments (exons).

In accordance with an aspect of the present invention, there is provided an isolated nucleic acid (polynucleotide) Which encodes for the mature polypeptide having the deduced amino acid sequence of FIG. 1 (SEQ. ID NO: 2) or for the mature polypeptide encoded by the cDNA of the clone deposited at the American Type Culture Collection (ATCC), Patent Depository, 10801 University Boulevard, Manassas, Va. 20110-2209; as ATCC Deposit No. 75899 on Sep. 29, 1994.

A polynucleotide encoding a polypeptide of the present invention may be obtained from human pulmonary tissue, hippocampus and adult heart. The polynucleotide of this invention was discovered in a cDNA library derived from human early passage fibroblasts (HSA 172 cells). It is structurally related to the human TNF-R2 receptor. It contains an open reading frame encoding a protein of 401 amino acid residues of which approximately the first 21 amino acids residues are the putative leader sequence such that the mature protein comprises 380 amino acid. Six conserved cyteines present in modules of 40 residues in all TNF receptors are conserved in this receptor.

The TNF receptor of the present invention is a soluble receptor and is secreted, however, it may also exist as a membrane bound receptor having a transmembrane region and an intra- and extracellular region. The polypeptide of the present invention may bind TNF and lymphotoxin ligands.

In accordance with an aspect of the present invention there is provided a polynucleotide which may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1 (SEQ ID No: 1) or that of the deposited clone or may be a different coding sequence which coding sequence, as a result of the redundancy or degeneracy of the genetic code, encodes the same mature polypeptide as the DNA of FIG. 1 (SEQ ID No: 1) or the deposited cDNA.

The polynucleotide which encodes for the mature polypeptide of FIG. 1 (SEQ ID No. 2) or for the mature polypeptide encoded by the deposited cDNA may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1 (SEQ ID No: 2) or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIG. 1 (SEQ ID No: 2) or the same mature polypeptide encoded by the cDNA of the deposited clone as well as variants of such polynucleotides which variants encode for a fragment, derivative or analog of the polypeptide of FIG. 1 (SEQ ID No: 2) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIG. 1 (SEQ ID No: 1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature protein, or for a protein having a prosequence or for a protein having both a prosequence and a presequence (leader sequence).

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)). The coding sequence may also be fused to a sequence which codes for a fusion protein such as an IgG Fc fusion protein.

The term "gene" means the segment of DNA involved in producing a polypeptide chain; it includes regions preceding and following the coding region (leader and trailer) as well as intervening sequences (introns) between individual coding segments (exons).

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIG. 1 (SEQ ID NO:1) or the deposited cDNA(s).

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2 as well as fragments thereof, which fragments have at least 30 bases and preferably at least 50 bases and to polypeptides encoded by such polynucleotides. The deposit(s) referred to herein will be maintained under the terms of the Budapest Treaty on the International Recognition of the Deposit of Microorganism for purposes of Patent Procedure. These deposits are provided merely as convenience to those of skill on the art and are not an admission that a deposit is required under 35 U.S.C. §112. The sequence of the polynucleotides contained In the deposited materials, as well as the amino acid sequence of the polypeptides encoded thereby, are incorporated herein by reference and are controlling in the event of any conflict with any description of sequences herein. A. license may be required to make, use or sell the deposited materials, and no such license is hereby granted.

The present invention further relates to a polypeptide which has the deduced amino acid sequence of FIG. 1 (SEQ ID No. 2) or which has the amino acid sequence encoded by the deposited cDNA, as well as fragments, analogs and derivatives of such polypeptide.

The terms "fragment," "derivative" and "analog" when referring to the polypeptide of FIG. 1 (SEQ ID No. 2) or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIG. 1 (SEQ ID No. 2) or that encoded by the deposited cDNA may be (i)-one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IbG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 (in particular the mature polypeptide) as well as polypeptides which have at least 70% similarity (preferably at least 70% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 90% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the nucleic acid sequences of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudo-rabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli.* lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli.*

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli, Streptomyces, Salmonella typhimurium;* fungal cells, such as yeast; insect cells such as *Drosophila S2* and *Spodoptera Sf9*; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pBS, pD10, phagescript, psiX174, pbluescript SK, pbsks, pNH8A, pNH16a, pNH18A, pNH46A (Stratagene); pTRC99a, pKK223-3, pKK233-3, pDR540, pRIT5 (Pharmacia). Eukaryotic: pWLNEO, pSV2CAT, pOG44, pXT1, pSG (Stratagene) pSVK3, PBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40 LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKR223–3 (Pharmacia Fine Chemicals, Uppsala, Sweden) and GEMI (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptide of the present invention can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The TNF receptor of the present invention was assayed for the ability to bind TNF-α and TNF-β, however, the present invention also contemplates the ability of the receptor to bind other TNF-like proteins. Monoclonal antibodies specific to TNF-α and TNF-β were prepared. These monoclonal antibodies were bound to TNF-α and TNF-β and a control ELISA assay was performed to quantify the amount of monoclonal antibody present. The TNF receptor was then bound to TNF-α and TNF-β in the same way in which the monoclonal antibody was bound and another BLISA assay was performed. The TNF receptor was found to bind to TNF-β just as strongly as the monoclonal antibody, while it only bound TNF-α two-thirds as strongly.

Fragments of the full length polynucleotide sequences of the present invention may be used as a hybridization probe for a cDNA library to isolate other genes which have a high sequence similarity to the polynucleotide sequence of the present invention or similar biological activity. Probes of this type generally have at least 50 bases, although they may have a greater number of bases. The probe may also be used as markers to identify a cDNA clone corresponding to a full length transcript and a genomic clone or clones that contain the complete polynucleotide sequence of the present invention including regulatory and promotor regions, exons, and introns. An example of a screen comprises isolating the coding region of the gene of the present invention by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

This invention also provides a method of screening compounds to identify compounds which interact with the polypeptide of the present invention which comprises contacting a mammalian cell comprising an isolated DNA molecule encoding and expressing a the polypeptide of the present invention with a plurality of compounds, determining those which activate or block the activation of the receptor, and thereby identifying compounds which specifically interact with, and activate or block the activation of the polypeptide of the present invention.

This invention also contemplates the use of the polynucleotide of the present invention as a diagnostic. For example, if a mutation is present, conditions would result from a lack of TNF receptor activity. Further, mutations which enhance TNF receptor activity would lead to diseases associated with an over-expression of the receptor, e.g., endotoxic shock. Mutated genes can be detected by comparing the sequence of the defective gene with that of a normal one. Subsequently one can verify that a mutant gene is associated with a disease condition or the susceptibility to a disease condition. That is, a mutant gene which leads to the underexpression of the TNF receptor would be associated with an inability of TNF to inhibit tumor growth.

Individuals carrying mutations in the polynucleotide of the present invention may be detected at the DNA level by a variety of techniques. Nucleic acids used for diagnosis may be obtained from a patient's cells which include, but are not limited to, blood, urine, saliva and tissue biopsy. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid of the instant invention can be used to identify and analyze gene mutations. For example, deletions and insertions can be detected by a change in the size of the amplified product in comparison to the normal genotype. Point mutations can be identified by hybridizing amplified DNA to radiolabeled RNA or alternatively, radiolabeled TNP receptor antisense DNA sequences. Perfectly matched sequences can be distinguished from mismatched duplexes by RNase A digestion or by differences in melting temperatures. Such a diagnostic would be particularly useful for prenatal or even neonatal testing.

Sequence differences between the reference gene and "mutants" may be revealed by the direct DNA sequencing method. In addition, cloned DNA segments may be used as probes to detect specific DNA segments. The sensitivity of this method is greatly enhanced when combined with PCR. For example, a sequencing primary used with double stranded PCR product or a single stranded template molecule generated by a modified PCR product. The sequence determination is performed by conventional procedures with radiolabeled nucleotides or by automatic sequencing procedures with fluorescent tags.

Sequence changes at the specific locations may be revealed by nuclease protection assays, such as RNase and S1 protection or the chemical cleavage method (for example, Cotton et al., PNAS, 85:4397–4401 (1985)).

The present invention further relates to a diagnostic assay which detects an altered level of a soluble form of the polypeptide of the present invention where an elevated level in a sample derived from a host is indicative of certain diseases. Assays available to detect levels of soluble receptors are well known to those of skill in the art, for example, radioimmunoassays, competitive-binding assays, Western blot analysis, and preferably an ELISA assay may be employed.

An ELISA assay initially comprises preparing an antibody specific to an antigen to the polypeptide of the present invention, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a non-specific protein such as bovine serum albumen. Next, the monoclonal antibody is incubated in the dish during which time the monoclonal antibodies attach to any proteins of the present invention which are attached to the polystyrene dish. All unbound monoclonal antibody is washed out with buffer. The reporter antibody linked to horseradish peroxidase is now placed in the dish resulting in binding of the reporter antibody to any monoclonal antibody bound to the polypeptide of the present invention. Unattached reporter antibody is then washed out. Peroxidase substrates are then added to the dish and the amount of color developed in a given time period is a measurement of the amount of the protein of interest present in a given volume of patient sample when compared against a standard curve.

A competition assay may be employed wherein antibodies specific to the polypeptides of the present invention are attached to a solid support. Labeled TNF receptor polypeptides, and a sample derived from the host are passed over the solid support and the amount of label detected attached to the solid support can be correlated to a quantity in the sample. The soluble form of the receptor may also be employed to identify agonists and antagonists.

A thymocyte proliferation assay may be employed to identify both ligands and potential agonists and antagonists to the polypeptide of the present invention. For example, thymus cells are disaggregated from tissue and grown in culture medium. Incorporation of DNA prescursors such as $^3$H-thymidine or 5-bromo-2'-deoxyuridine (BrdU) is monitored as a parameter for DNA synthesis and cellular proliferation. Cells which have incorporated BrdU into DNA can be detected using a monoclonal antibody against BrdU and measured by an enzyme or fluorochrome-conjugated second antibody. The reaction is quantitated by fluorimetry or by spectrophotometry. Two control wells and an experimental well are set up. TNF-β added to all wells, while soluble receptors of the present invention are added to the experimental well. Also added to the experimental well is a compound to be screened. The ability of the compound to be screened to inhibit the interaction of TNF-β with the receptor polypeptides of the present invention may then be quantified. In the case of the agonists, the ability of the compound to enhance this interaction is quantified.

A determination may be made whether a ligand not known to be capable of binding to the polypeptide of the present invention can bind thereto comprising contacting a mammalian cell comprising an isolated molecule encoding a polypeptide of the present invention with a ligand under conditions permitting binding of ligands known to bind thereto, detecting the presence of any bound ligand, and thereby determining whether such ligands bind to a polypeptide of the present invention. Also, a soluble form of the receptor may utilized in the above assay where it is secreted in to the extra-cellular medium and contacted with ligands to determine which will bind to the soluble form of the receptor.

Other agonist and antagonist screening procedures involve providing appropriate cells which express the receptor on the surface thereof. In particular, a polynucleotide encoding a polypeptide of the present invention is employed to transfect cells to thereby express the polypeptide. Such transfection may be accomplished by procedures as hereinabove described.

Thus, for example, such assay may be employed for screening for a receptor antagonist by contacting the cells which encode the polypeptide of the present invention with both the receptor ligand and a compound to be screened. Inhibition of the signal generated by the ligand indicates that a compound is a potential antagonist for the receptor, i.e., inhibits activation of the receptor.

The screening may be employed for determining an agonist by contacting such cells with compounds to be screened and determining whether such compounds generate a signal, i.e., activates the receptor.

Other screening techniques include the use of cells which express the polypeptide of the present invention (for example, transfected CHO cells) in a system which measures extracellular pH changes caused by receptor activation, for example, as described in Science, Volume 246, pages 181–296 (1989). In another example, potential agonists or antagonists may be contacted with a cell which expresses the polypeptide of the present invention and a second messenger response, e.g., signal transduction may be measured to determine whether the potential antagonist or agonist is effective.

Another screening technique involves expressing the receptor polypeptide wherein it is linked to phospholipase C or D. As representative examples of such cells, there may be mentioned endothelial cells, smooth muscle cells, embryonic kidney cells and the like. The screening for an antagonist or agonist may be accomplished as hereinabove described by detecting activation of the receptor or inhibition of activation of the receptor from the phospholipase second signal.

Antibodies may be utilized as both an agonist and antagonist depending on which part of the polypeptide of the present invention the antibody binds to. The antibody in one instance can bind to the active site and block ligand access. However, it has been observed that monoclonal antibodies directed against certain TNF receptors can act as specific agonists when binding to the extra-cellular domain of the receptor.

In addition to the antagonists identified above, oligonucleotides which bind to the TNF receptor may also act as TNF receptor antagonists. Alternatively, a potential TNF receptor antagonist may be a soluble form of the TNF receptor which contains the complete extra-cellular region of the TNF receptor and which binds to ligands to inhibit their biological activity.

Another potential TNF receptor antagonist is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251: 1360 (1991)), thereby preventing transcription and the production of TNF receptors. The antisense RNA oligonucleotide hybridizes to the mRNA in vivo and blocks translation of the mRNA molecule into the TNF receptor polypeptide (antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of TNF receptors.

TNF receptor antagonists also include a small molecule which binds to and occupies the TNF receptor thereby making the receptor inaccessible to ligands which bind thereto such that normal biological activity is prevented. Examples of small molecules include but are not limited to small peptides or peptide-like molecules.

The TNF receptor agonists may be employed to stimulate ligand activities, such as inhibition of tumor growth and necrosis of certain transplantable tumors. The agonists may also be employed to stimulate cellular differentiation, for example, T-cell, fibroblasts and haemopoietic cell differentiation. Agonists to the TNF receptor may also augment TNF's role in the host's defense against microorganisms and prevent related diseases (infections such as that from *L. monocytogenes*) and chlamidiae. The agonists may also be employed to protect against the deleterious effects of ionizing radiation produced during a course of radiotherapy, such as denaturation of enzymes, lipid peroxidation, and DNA damage.

The agonists may also be employed to mediate an antiviral response, to regulate growth, to mediate the immune response and to treat immunodeficiencies related to diseases such as HIV.

Antagonists to the TNF receptor may be employed to treat autoimmune diseases, for example, graft versus host rejection and allograft rejection, and T-cell mediated autoimmune diseases such as AIDS. It has been shown that T-cell proliferation is stimulated via a type 2 TNP receptor. Accordingly, antagonizing the receptor may prevent the proliferation of T-cells and treat T-cell mediated autoimmune diseases.

The antagonists may also be employed to prevent apoptosis, which is the basis for diseases such as viral infection, rheumatoid arthritis, systemic lupus erythematosus, insulin-dependent diabetes mellitus, and graft rejection. Similarly, the antagonists may be employed to prevent cytotoxicity.

The antagonists to the TNF receptor may also be employed to treat B cell cancers which are stimulated by TNF.

Antagonists to the TNF receptor may also be employed to treat and/or prevent septic shock, which remains a critical clinical condition. Septic shock results from an exaggerated host response, mediated by protein factors such as TNF and IL-1, rather than from a pathogen directly. For example, lipopolysaccharides have been shown to elicit the release of TNF leading to a strong and transient increase of its serum concentration. TNF causes shock and tissue injury when administered in excessive amounts. Accordingly, antagonists to the TNF receptor will block the actions of TNF and treat/prevent septic shock. These antagonists may also be employed to treat meningococcemia in children which correlates with high serum levels of TNF.

Among other disorders which may be treated by the antagonists to TNF receptors, there are included, inflammation which is mediated by TNF receptor ligands, and the bacterial infections cachexia and cerebral malaria. TNF receptor antagonists may also be employed to treat inflammation mediated by ligands to the receptor such as TNF.

The soluble TNF receptor and agonists and antagonists may be employed in combination with a suitable pharmaceutical carrier. Such compositions comprise a therapeutically effective amount of the soluble receptor or agonist or antagonist, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such containers can be a notice in the form prescribed by a governmental agency regulating the manufacture, use or sale of pharmaceuticals or biological products, which notice reflects approval by the agency of manufacture, use or sale for human administration. In addition, the soluble form of the receptor and agonists and antagonists of the present invention may also be employed in conjunction with other therapeutic compounds.

The pharmaceutical compositions may be administered in a convenient manner such as by the oral, topical, intravenous, intraperitoneal, intramuscular, subcutaneous, intranasal or intradermal routes. The pharmaceutical compositions are administered in an amount which is effective for treating and/or prophylaxis of the specific indication. In general, they are administered in an amount of at least about 10 μg/kg body weight and in most cases they will be administered in an amount not in excess of about 8 mg/Kg body weight per day. In most cases, the dosage is from about 10 μg/kg to about 1 mg/kg body weight daily, taking into account the routes of administration, symptoms, etc.

The TNF receptor and agonists and antagonists which are polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells. The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., .1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 μg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1
Bacterial Expression and Purification of the TNF Receptor

The DNA sequence encoding TNF receptor, ATCC #75899, is initially amplified using PCR oligonucleotide primers corresponding to the 5' and 3' end sequences of the processed TNF receptor nucleic acid sequence (minus the signal peptide sequence). Additional nucleotides corresponding to TNF receptor gene are added to the 5' and 3' end sequences respectively. The 5' oligonucleotide primer has the sequence 5' GCCAGAGGATCCGAAACGTTTCCTCCAAAGTAC 3' (SEQ ID No: 4) contains a BamHI restriction enzyme site (bold) followed by 21 nucleotides of TNF receptor coding sequence starting from the presumed initiation codon. The 3' sequence 5' CGGCTTCTAGAATTACCTATCATTTCTAAAAAT 3' (SEQ ID No: 5) contains complementary sequences to a Hind III site (bold) and is followed by 18 nucleotides of TNF receptor. The restriction enzyme sites correspond to the restriction enzyme sites on the bacterial expression vector pQE-9 (Qiagen, Inc. Chatsworth, Calif.). pQE-9 encodes antibiotic resistance (Amp'), a bacterial origin of replication (ori), an IPTG-regulatable promoter operator (P/o), a ribosome binding site (RBS), a 6-His tag and restriction enzyme sites. pQE-9 is then digested with BamHI and XbaI. The amplified sequences are ligated into pQE-9 and are inserted in frame with the sequence encoding for the histidine tag and the RBS. The ligation mixture is then used to transform E. coli strain M15/rep 4 (Qiagen, Inc.) by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance (Kan'). Transformants are identified by their ability to grow on LB plates and ampicillin/kanamycin resistant colonies are selected. Plasmid DNA is isolated and confirmed by restriction analysis. Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG ("Isopropyl-B-D-thiogalacto pyranoside") is then added to a final concentration of 1 mM. IPTG induces by inactivating the lacI repressor, clearing the P/O leading to increased gene expression. Cells are grown an extra 3 to 4 hours. Cells are then harvested by centrifugation. The cell pellet is solubilized in the chaotropic agent 6 Molar Guanidine HCl. After clarification, solubilized TNF receptor is purified from this solution by chromatography on a Nickel-Chelate column under conditions that allow for tight binding by proteins containing the 6-His tag (Hochuli, B. et al., J. Chromatography 411:177–184 (1984)). TNF receptor (90% pure) is eluted from the column in 6 molar guanidine HCl pH 5.0 and for the purpose of renaturation adjusted to 3 molar guanidine HCl, 100 mM sodium phosphate, 10 molar glutathione (reduced) and 2 mmolar glutathione (oxidized). After incubation in this solution for 12 hours the protein is dialyzed to 10 mmolar sodium phosphate.

EXAMPLE 2
Cloning and Expression of TNF Receptor and Extracellular (Soluble) TNF Receptor Using the Baculovirus Expression System The DNA sequence encoding the full length TNF receptor protein, ATCC #75899, was amplified using PCR oligonucleotide primers corresponding to the 5' and 3'sequences of the gene. The 5' primer has the sequence 5' GCGCG-GATCCATGAACAAGTTGCTGTGCTGC 3' (SEQ ID No: 6) and contains a BamHI restriction enzyme site (in bold) and which is just behind the first 21 nucleotides of the TNF receptor gene (the initiation codon for translation "ATG" is underlined).

The 3' primer has the sequence 5' GCGCTCTAGATTACCTATCATTTCTAAAAATAAC 3' (SEQ ID No: 7) ad 5'GCGCGGTACCTCAGTGGTTTGGGCTCCTCCC 3' (SEQ ID No: 8) and contains the cleavage site for the restriction endonuclease XbaI and 21 nucleotides complementary to the 3' non-translated sequence of the TNF receptor gene. The amplified sequences were isolated from a 1% agarose gel using a commercially available kit ("Geneclean", BIO 101 Inc., La Jolla, Calif.). The fragments were then digested with the endonucleases BamHI and XbaI and then purified again on a 1% agarose gel. This fragment is designated F2.

The vector pRG1 (modification of pVL941 vector, discussed below) was used for the expression of the TNF receptor proteins using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa californica nuclear polyhedrosis virus (AcMNPV) followed by the recognition sites for the restriction endonucleases BamHI and XbaI. The polyadenylation site of the simian virus (SV)40 was used for efficient polyadenylation. For an easy selection of recombinant viruses the beta-galactosidase gene from E. coli was inserted in the same orientation as the polyhedrin promoter followed by the polyadenylation signal of the polyhedrin gene. The polyhedrin sequences were flanked at both sides by viral sequences for the cell-mediated homologous recombination of cotransfected wild-type viral DNA. Many other baculovirus vectors could be used in place of pRG1 such as pAc373, pVL941 and pAcIM1 (Luckow, V. A. and Summers, M. D., Virology, 170:31–39).

The plasmid was digested with the restriction enzymes BamHI and XbaI. The DNA was then isolated from a 1% agarose gel using the commercially available kit ("Geneclean" BIO 101 Inc., La Jolla, Calif.). This vector DNA is designated V2.

Fragment F2 and the dephosphorylated plasmid V2 were ligated with T4. DNA ligase. *E. coli* HB101 cells were then transformed and cells identified that contained the plasmid (pBac TNF receptor) with the TNF receptor genes using the enzymes BamHI and XbaI. The sequence of the cloned fragment was confirmed by DNA sequencing.

5 μg of the plasmid pBac TNF receptor was cotransfected with 1.0 μg of a commercially available linearized baculovirus ("BaculoGold™ baculovirus DNA", Pharmingen, San Diego, Calif.) using the lipofection method (Felgner et al. Proc. Natl. Acad. Sci. USA, 84:7413–7417 (1987)).

1 μg of BaculoGold™ virus DNA and 5 μg of the plasmid pBac TNF receptors were mixed in a sterile well of a microtiter plate containing 50 μl of serum free Grace's medium (Life Technologies Inc., Gaithersburg, Md.). Afterwards 10 μl Lipofectin plus 90 μl Grace's medium were added, mixed and incubated for 15 minutes at room temperature. Then the transfection mixture was added dropwise to the Sf9 insect cells (ATCC CRL 1711) seeded in a 35 mm tissue culture plate with 1 ml Grace' medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation continued at 27° C. for four days.

After four days the supernatant was collected and a plaque assay performed similar as described by Summers and Smith (supra). As a modification an agarose gel with "Blue Gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the viruses were added to the cells and blue stained plaques were picked with the tip of an Eppendorf pipette. The agar containing the recombinant viruses were then resuspended in an Eppendorf tube containing 200 μl of Grace's medium. The agar was removed by a brief centrifugation and the supernatant containing the recombinant baculoviruses was used to infect Sf9 cells seeded in 35 mm dishes. Four days later the supernatants of these culture dishes were harvested and then stored at 4+ C.

Sf9 cells were grown in Grace's medium supplemented with 10% heat-inactivated FBS. The cells were infected with the recombinant baculovirus V-TNF receptor at a multiplicity of infection (MOI) of 2. Six hours later the medium was removed and replaced with SP900 II medium minus methionine and cysteine (Life Technologies Inc., Gaithersburg). 42 hours later 5 μCi of $^{35}$S-methionine and 5 μCi $^{35}$S cysteine (Amersham) were added. The cells are further incubated for 16 hours before they are harvested by centrifugation and the labelled proteins visualized by SDS-PAGE and autoradiography.

EXAMPLE 3
Expression of Recombinant TNF Receptor in COS Cells

The expression of plasmid, TNF receptor HA is derived from a vector pcDNAI/Amp (Invitrogen) containing: 1) SV40 origin of replication, 2) ampicillin resistance gene, 3) *E. coli* replication origin, 4) CMV promoter followed by a polylinker region, a SV40 intron and polyadenylation site. A DNA fragment encoding the entire TNF receptor precursor and a HA tag fused in frame to its 3' end is cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lerner, 1984, Cell 37, 767). The infusion of HA tag to the target protein allows easy detection of the recombinant protein with an antibody that recognizes the HA epitope.

The plasmid construction strategy is described as follows:

The DNA sequence encoding TNF receptor, ATCC #75899, is constructed by PCR using two primers: the 5' primer 5' GCCAGAGGATCCGCCACCATGAACAAGT-TGCTGTGCTGC 3' (SEQ ID No. 8) contains a BamHI site (bold) followed by 21 nucleotides of TNF receptor coding sequence starting from the initiation codon; the 3' sequence 5' CGGCTTCTAGAATCAAGCGTAGTCTGGGACG TCGTATGGGTACCTATCATTTCTAAAAAT 3' (SEQ ID No. 9) contains complementary sequences to an XbaI site (bold), translation stop codon, HA tag and the last 18 nucleotides of the TNF receptor coding sequence (not including the stop codon). Therefore, the PCR product contains a BamHI site, TNF receptor coding sequence followed by HA tag fused in frame, a translation termination stop codon next to the HA tag, and an XbaI site. The PCR amplified DNA fragment and the vector, pcDNAI/Amp, are digested with BamHI and XbaI restriction enzymes and ligated. The ligation mixture is transformed into *E. coli* strain SURE (Stratagene Cloning Systems, La Jolla, Calif.) the transformed culture is plated on ampicillin media plates and resistant colonies are selected. Plasmid DNA is isolated from transformants and examined by restriction analysis for the presence of the correct fragment. For expression of the recombinant TNF receptor, COS cells are transfected with the expression vector by DEAE-DEXTRAN method (J. Sambrook, B. Fritsch, T. Maniatis, Molecular Cloning: A Laboratory Manual, Cold Spring Laboratory Press, (1989)). The expression of the TNF receptor HA protein is detected by radiolabelling and immunoprecipitation method (E. Harlow, D. Lane, Antibodies: A Laboratory Manual, Cold Spring Harbor Laboratory Press, (1988)). Cells are labelled for 8 hours with $^{35}$S-cysteine two days post transfection. Culture media are then collected and cells are lysed with detergent (RIPA buffer (150 mM NaCl, 1% NP-40, 0.1% SDS, 1% NP-40, 0.5% DOC, 50 mM Tris, pH 7.5) (Wilson, I. et al., Id. 37:767 (1984)). Both cell lysate and culture media are precipitated with a HA specific monoclonal antibody. Proteins precipitated are analyzed on 15% SDS-PAGE gels.

EXAMPLE 4
Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer further includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product. Numerous modifications and variations of the present invention are possible in light of the above teachings and, therefore, within the scope of the appended claims, the invention may be practiced otherwise than as particularly described.

What is claimed is:

1. An isolated polynucleotide comprising the polynucleotide recited in SEQ ID NO:1.

2. An isolated nucleic acid molecule comprising a polynucleotide selected from the group consisting of:
   (a) a polynucleotide encoding amino acids −21 to 380 of SEQ ID NO:2;
   (b) a polynucleotide encoding amino acids −20 to 380 of SEQ ID NO:2;
   (c) a polynucleotide encoding amino acids 1 to 380 of SEQ ID NO:2;
   (d) the complement of (a);
   (e) the complement of (b); and
   (f) the complement of (c).

3. The isolated nucleic acid molecule of claim 2, wherein said polynucleotide is (a).

4. The isolated nucleic acid molecule of claim 2, wherein said polynucleotide is (b).

5. The isolated nucleic acid molecule of claim 2, wherein said polynucleotide is (c).

6. The isolated nucleic acid molecule of claim 2, wherein said polynucleotide is (d).

7. The isolated nucleic acid molecule of claim 2, wherein said polynucleotide is (e).

8. The isolated nucleic acid molecule of claim 2, wherein said polynucleotide is (f).

9. The isolated nucleic acid molecule of claim 3, which comprises nucleotides 46 to 1248 of SEQ ID NO:1.

10. The isolated nucleic acid molecule of claim 4, wherein comprises nucleotides 49 to 1248 of SEQ ID NO:1.

11. The isolated nucleic acid molecule of claim 5, which comprises nucleotides 109 to 1248 of SEQ ID NO:1.

12. The isolated nucleic acid molecule of claim 2, which is DNA.

13. The isolated nucleic acid molecule of claim 9, which is DNA.

14. The isolated nucleic acid molecule of claim 10, which is DNA.

15. The isolated nucleic acid molecule of claim 11, which is DNA.

16. The isolated nucleic acid molecule of claim 2, which is RNA.

17. The isolated nucleic acid molecule of claim 9, which is RNA.

18. The isolated nucleic acid molecule of claim 10, which is RNA.

19. The isolated nucleic acid molecule of claim 11, which is RNA.

20. The isolated nucleic acid molecule of claim 2, which is fused to a polynucleotide encoding a heterologous protein.

21. A method of making a recombinant vector comprising inserting the nucleic acid molecule of claim 2 into a vector.

22. A recombinant vector produced by the method of claim 21.

23. A genetically engineered host cell that contains the nucleic acid molecule of claim 2.

24. A genetically engineered host cell that contains the polynucleotide of claim 2 operatively associated with a regulatory sequence that controls gene expression.

25. A recombinant method for producing a polypeptide, comprising culturing the host cell of claim 24 under conditions such that said polypeptide is expressed and recovering said polypeptide.

26. An isolated nucleic acid molecule comprising a polynucleotide selected from the group consisting of:
   (a) a polynucleotide encoding mature Tumor Necrosis Factor Receptor polypeptide as encoded by the cDNA in ATCC Deposit No. 75899; and
   (b) the complement of (a).

27. The isolated nucleic acid molecule of claim 26, wherein said polynucleotide is (a).

28. The isolated nucleic acid molecule of claim 26, wherein said polynucleotide is (b).

29. The isolated nucleic acid molecule of claim 27, which comprises DNA identical to the coding portion of the cDNA in ATCC Deposit No. 75899.

30. An isolated nucleic acid molecule comprising 1 contiguous nucleotides of the coding region of the cDNA in ATCC Deposit No. 75899.

31. The isolated nucleic acid molecule of claim 30, which comprises 50 contiguous nucleotides of the coding region of the cDNA in ATCC Deposit No. 75899.

32. An isolated nucleic acid molecule encoding a polypeptide comprising 30 contiguous amino acids encoded by the cDNA in ATCC Deposit No. 75899.

33. The isolated nucleic acid molecule of claim 32, which encodes a polypeptide comprising 50 contiguous amino acids encoded by the cDNA in ATCC Deposit No. 75899.

34. An isolated nucleic acid molecule comprising 30 contiguous nucleotides of the coding region of SEQ ID NO:1.

35. The isolated nucleic acid molecule of claim 34, which comprises 50 contiguous nucleotides of the coding region of SEQ ID NO:1.

36. An isolated nucleic acid molecule encoding a polypeptide comprising 30 contiguous amino acids of SEQ ID NO:2.

37. The isolated nucleic acid molecule of claim 36, which encodes a polypeptide comprising 50 contiguous amino acids of SEQ ID NO:2.

38. The isolated nucleic acid molecule of claim 36, wherein said polypeptide binds a member selected from the group consisting of:
   (a) tumor necrosis factor α;
   (b) tumor necrosis factor β; and
   (c) an antibody having specificity for the polypeptide of SEQ ID NO:2.

39. The isolated nucleic acid molecule of claim 37, wherein said polypeptide binds a member selected from the group consisting of:
   (a) tumor necrosis factor α;
   (b) tumor necrosis factor β; and
   (c) an antibody having specificity for the polypeptide of SEQ ID NO:2.

40. The isolated nucleic acid molecule of claim 38, wherein said member is (a).

41. The isolated nucleic acid molecule of claim 38, wherein said member is (b).

42. The isolated nucleic acid molecule of claim 38, wherein said member is (c).

43. The isolated nucleic acid molecule of claim 38, wherein said member is (a).

44. The isolated nucleic acid molecule of claim 39, wherein said member is (b).

45. The isolated nucleic acid molecule of claim 39, wherein said member is (c).

46. The isolated nucleic acid molecule of claim 34, which is fused to a polynucleotide encoding a heterologous protein.

47. A method of making a recombinant vector comprising inserting the nucleic acid molecule of claim 34 into a vector.

48. A recombinant vector produced by the method of claim 47.

49. A genetically engineered host cell that contains the nucleic acid molecule of claim 48.

50. A genetically engineered host cell that contains the polynucleotide of claim 34 operatively associated with a regulatory sequence that controls gene expression.

51. A recombinant method for producing a polypeptide, comprising culturing the host cell of claim 50 under conditions such that said polypeptide is expressed and recovering said polypeptide.

* * * * *

UNITED STATES PATENT AND TRADEMARK OFFICE
CERTIFICATE OF CORRECTION

PATENT NO.         : 7,094,564 B1                                               Page 1 of 1
APPLICATION NO. : 08/469637
DATED              : August 22, 2006
INVENTOR(S)        : Greene et al.

It is certified that error appears in the above-identified patent and that said Letters Patent is hereby corrected as shown below:

In the Claims:

In Claim 30, delete "An isolated nucleic acid molecule comprising 1 contiguous nucleotides" and insert -- An isolated nucleic acid molecule comprising 30 contiguous nucleotides--;

In Claim 43, delete "The isolated nucleic acid molecule of claim 38," and insert -- The isolated nucleic acid molecule of claim 39, --.

Signed and Sealed this

Nineteenth Day of December, 2006

JON W. DUDAS
*Director of the United States Patent and Trademark Office*